US012324764B2

(12) United States Patent
Zhao et al.

(10) Patent No.: US 12,324,764 B2
(45) Date of Patent: Jun. 10, 2025

(54) VENTED NASAL PLUG

(71) Applicant: Ohio State Innovation Foundation, Columbus, OH (US)

(72) Inventors: Kai Zhao, Dublin, OH (US); Kanghyun Kim, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 220 days.

(21) Appl. No.: 17/801,154

(22) PCT Filed: Feb. 19, 2021

(86) PCT No.: PCT/US2021/018824
§ 371 (c)(1),
(2) Date: Aug. 19, 2022

(87) PCT Pub. No.: WO2021/168285
PCT Pub. Date: Aug. 26, 2021

(65) Prior Publication Data
US 2023/0072399 A1 Mar. 9, 2023

Related U.S. Application Data

(60) Provisional application No. 62/979,707, filed on Feb. 21, 2020.

(51) Int. Cl.
*A61F 5/08* (2006.01)
*A61M 16/06* (2006.01)
(52) U.S. Cl.
CPC ............ *A61F 5/08* (2013.01); *A61M 16/0672* (2014.02); *A61M 2210/0618* (2013.01)
(58) Field of Classification Search
CPC .......... A61F 5/08; A61F 5/56; A61F 13/2005; A61F 2/186; A61M 16/0672; A61M 16/0666; A61M 2210/0618; A61M 15/08
See application file for complete search history.

(56) References Cited

U.S. PATENT DOCUMENTS 2,569,743 A 10/1951 Pomeroy
2,674,245 A 4/1954 Tanditter
(Continued)

FOREIGN PATENT DOCUMENTS

CN 102949769 3/2013
WO 2014/104066 7/2014
(Continued)

OTHER PUBLICATIONS

Li, Chengyu, et al. "Nasal structural and aerodynamic features that may benefit normal olfactory sensitivity." Chemical senses 43.4 (2018): 229-237.
(Continued)

*Primary Examiner* — Katherine M Shi
*Assistant Examiner* — Mohammed S Adam
(74) *Attorney, Agent, or Firm* — Meunier Carlin & Curfman LLC

(57) ABSTRACT

A nasal plug includes a first tube having a first wall forming a first lumen of a first diameter. The first tube has a first tube proximal end in a proximal plane and a distal end in a distal plane. The nasal plug further includes a second tube that includes a second wall forming a second lumen of a second diameter, the second diameter smaller than the first diameter. A channel is formed by the second lumen and extends from the first tube proximal end into the first lumen of the first tube. The second tube also includes a flexible wall having a free end within the first lumen. The flexible wall is movable within the first lumen and has a length sufficient to touch a surface of the first lumen and fluidically seal the first lumen between the flexible wall and the surface of the first lumen. The second tube includes a channel proximal end in a channel proximal end plane. The channel proximal end plane is at an angle with respect to the distal plane of the first tube.

18 Claims, 11 Drawing Sheets

(56) References Cited

U.S. PATENT DOCUMENTS

| | | | |
|---|---|---|---|
| 3,935,859 | A | 2/1976 | Doyle |
| 5,105,807 | A | 4/1992 | Kahn et al. |
| 5,291,897 | A * | 3/1994 | Gastrin .............. A61M 16/085 |
| | | | 128/911 |
| 5,425,359 | A | 6/1995 | Nan-Tien |
| 5,601,594 | A | 2/1997 | Best |
| 6,478,026 | B1 | 11/2002 | Wood |
| 6,561,188 | B1 | 5/2003 | Ellis |
| 6,561,193 | B1 | 5/2003 | Noble |
| 6,848,446 | B2 | 2/2005 | Noble |
| 7,506,649 | B2 | 3/2009 | Doshi et al. |
| 7,727,186 | B2 | 6/2010 | Makower et al. |
| 7,856,979 | B2 | 12/2010 | Doshi et al. |
| 8,517,022 | B2 | 8/2013 | Halling et al. |
| 10,029,058 | B2 | 7/2018 | Foote et al. |
| 2004/0059368 | A1 | 3/2004 | Maryanka |
| 2009/0194100 | A1 | 8/2009 | Minagi |
| 2009/0308398 | A1 | 12/2009 | Ferdinand |
| 2012/0046607 | A1 | 2/2012 | Syk |
| 2012/0204870 | A1 * | 8/2012 | McAuley .......... A61M 16/0816 |
| | | | 128/207.18 |
| 2016/0128863 | A1 * | 5/2016 | Loomas .............. A61M 15/002 |
| | | | 128/848 |
| 2017/0119990 | A1 | 5/2017 | Vygon |
| 2018/0236201 | A1 | 8/2018 | Nussbaum et al. |
| 2020/0069321 | A1 | 3/2020 | Zhao |

FOREIGN PATENT DOCUMENTS

| | | |
|---|---|---|
| WO | 2018/165372 | 9/2018 |
| WO | 2021/168285 | 8/2021 |

OTHER PUBLICATIONS

Uldry, et al., Sniff nasal inspiratory pressure in patients with chronic obstructive pulmonary disease. Eur Respir J 1997; 10: 1292-1296.

Heritier, et al., Sniff nasal inspiratory pressure. A noninvasive assessment of inspiratory muscle strength. Am J Respir Crit Care Med vol. 150. 1994, pp. 1678-1683.

International Search Report and Written Opinion issued in PCT Application No. PCT/US2018/021464, dated Jun. 28, 2018.

International Preliminary Report on Patentability issued for Application No. PCT/US2018/021464, dated Sep. 19, 2019.

Zhao, Kai, et al. "Perceiving nasal patency through mucosal cooling rather than air temperature or nasal resistance." PLoS One 6.10 (2011): e24618.

International Preliminary Report on Patentability issued in PCT/US2021/018824, dated Sep. 1, 2022.

International Searching Authority (ISA/US). International Search Report and Written Opinion, issued n PCT Application No. PCT/US2021/018824 on May 19, 2021. 10 pages.

European Patent Office. Communication pursuant to Rule 164(1) EPC. Issued in European Application No. 21757729.5 on Feb. 16, 2024. 12 pages.

European Patent Office. Extended European Search Report. Issued in European Application No. 21757729.5 on May 8, 2024. 10 pages.

* cited by examiner

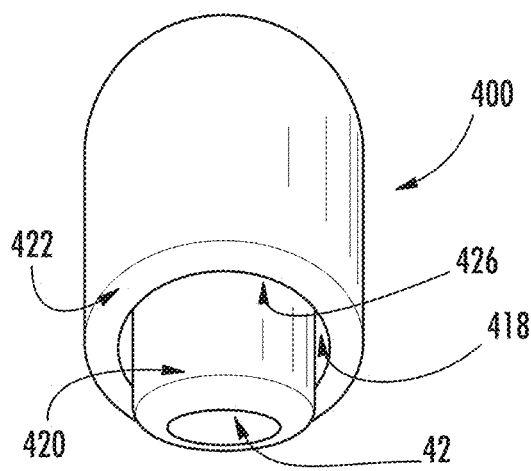
FIG. 4A
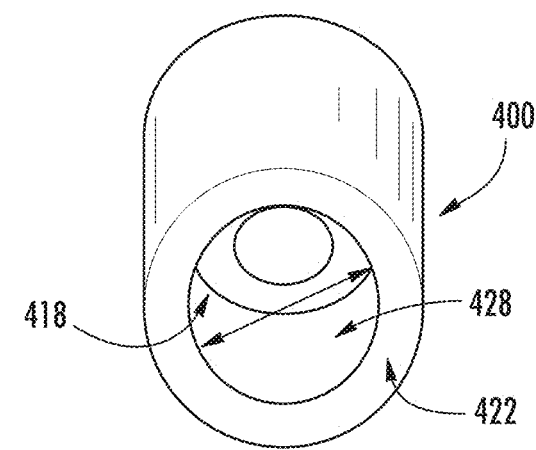
FIG. 4B
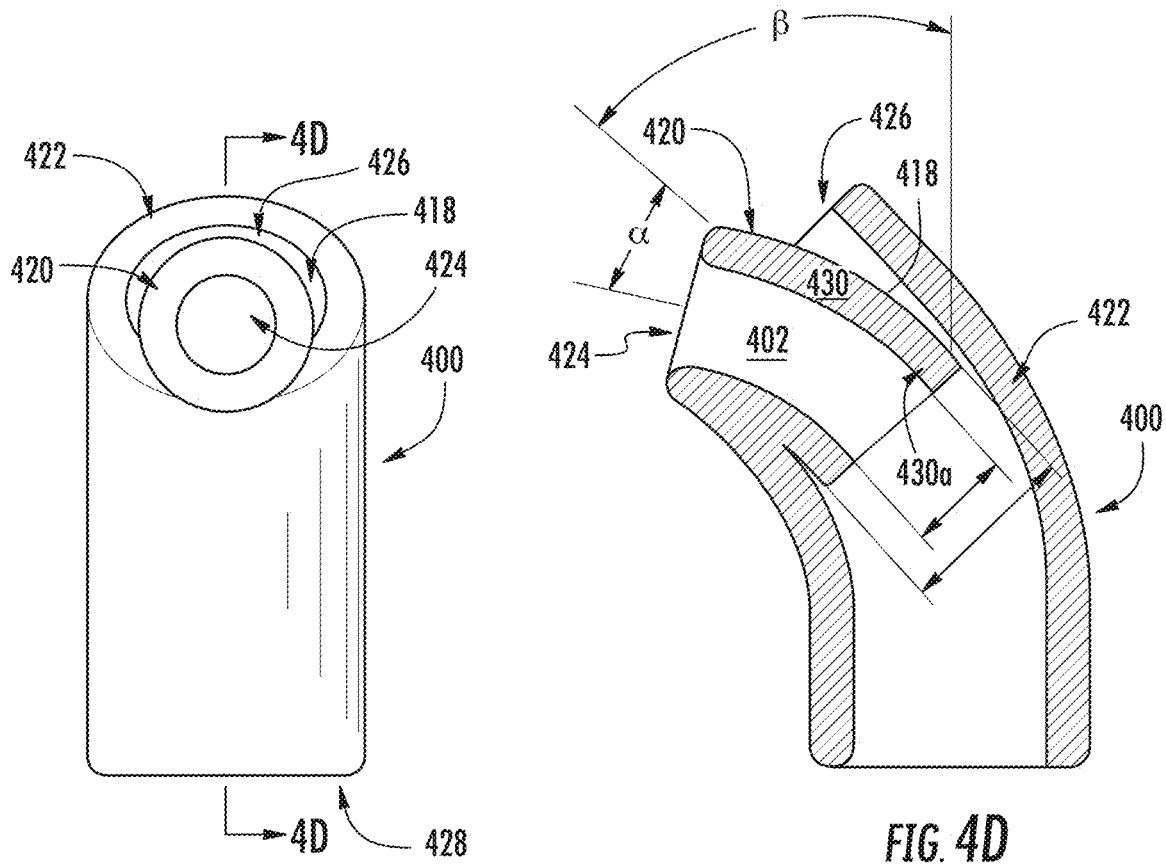
FIG. 4C
FIG. 4D

VENTED NASAL PLUG

CROSS REFERENCE TO RELATED APPLICATIONS

This application is a national stage application filed under 35 U.S.C. § 371 of PCT/US2021/018824 filed Feb. 19, 2021, which claims priority to U.S. Provisional Patent Application No. 62/979,707, filed Feb. 21, 2020, which application is hereby incorporated by this reference in its entirety as if fully set forth herein.

STATEMENT OF GOVERNMENT SUPPORT

This invention was made with government support under Grant R01 DC013626 awarded by the National Institutes of Health. The government has certain rights in the invention.

BACKGROUND OF THE INVENTION

Field of the Invention

Embodiments of the present invention relate to nasal plug, specifically a nasal plug providing a structure for differential capture of inflow and outflow.

Background

Nasal sinus disease is one of the most common medical conditions in the US, affecting an estimated 13% of adults, or some 30 million people. It accounts for 12.5 million physician office visits each year and an annual health expenditure of $5.8 billion (National Health Interview Survey 2009, CDC). It significantly impacts patient quality of life, even comparable to that of chronic debilitating diseases such as diabetes and congestive heart failure. Among its many symptoms, complaints of nasal obstruction is one of the primary symptoms that most significant impact a patient's quality of life. Many patients' nasal airflow patterns are disoriented, e.g. forming into a narrow jet. In fact, it is well known that patients' perception of nasal obstruction does not correlate to their nasal resistance, and could be due to irregular perception of nasal airflow, as discussed in "Perceiving Nasal Patency through Mucosal Cooling Rather than Air Temperature or Nasal Resistance," Zhao et al., PLoS ONE, Vol. 6, Issue 10, October 2011.

For example, Empty Nose Syndrome (ENS) is a rare but debilitating disease that occur after surgical therapy that supposedly treating their nasal sinus problems. Rather, following surgery, patients would have wide nasal airway (no obstruction), but still paradoxically complain of nasal obstruction. Other symptoms, including nasal crusting, dryness, nasal discharge, and nasal pain often accompany, or replace nasal obstruction. This syndrome can have a devastating impact on patients' quality of life: constant feeling of suffocation, elevated anxiety, disrupted concentration, chronic hyperventilation, chronic fatigue, severe sleeping difficulty and psychological disorders. Patients have committed suicide and committed murder on their physician as the results of the symptoms.

Accordingly, there is a need for treatment and relief of the person's perceived symptom of nasal obstruction beyond nasal resistance.

Prior art nasal plugs do not address the issues with disoriented nasal airflow patterns as well as empty nose syndrome because they are designed to merely prop open or dilate the nostrils. An example related art device meant for dilating the nostrils is shown in FIG. 1.

SUMMARY OF THE INVENTION

In accordance with the purpose(s) of this invention, as embodied and broadly described herein, this invention, in one aspect, relates to a nasal plug that includes a first tube having a first wall forming a first lumen of a first diameter. The first tube has a first tube proximal end in a proximal plane and a distal end in a distal plane. The nasal plug further includes a second tube that includes a second wall forming a second lumen of a second diameter, the second diameter smaller than the first diameter. A channel is formed by the second lumen and extends from the first tube proximal end into the first lumen of the first tube. The second tube also includes a flexible wall having a free end within the first lumen. The flexible wall is movable within the first lumen and has a length sufficient to touch a surface of the first lumen and fluidically seal the first lumen between the flexible wall and the surface of the first lumen. The second tube includes a channel proximal end in a channel proximal end plane. The channel proximal end plane is at an angle with respect to the distal plane of the first tube.

In another aspect, the invention relates to a kit comprising two nasal plugs where each nasal plug includes a first tube having a first wall forming a first lumen of a first diameter. The first tube has a first tube proximal end in a proximal plane and a distal end in a distal plane. The nasal plug further includes a second tube that includes a second wall forming a second lumen of a second diameter, the second diameter smaller than the first diameter. A channel is formed by the second lumen and extends from the first tube proximal end into the first lumen of the first tube. The second tube also includes a flexible wall having a free end within the first lumen. The flexible wall is movable within the first lumen and has a length sufficient to touch a surface of the first lumen and fluidically seal the first lumen between the flexible wall and the surface of the first lumen. The second tube includes a channel proximal end in a channel proximal end plane. The channel proximal end plane is at an angle with respect to the distal plane of the first tube.

In yet another aspect, the invention relates to a nasal plug that include a deformable plug having a first end and a second end and a cross-section sized and shaped to be accepted into and to fluidically seal a person's nasal nares; an axis defined from the first end to the second end. The plug includes a passage defined through the deformable polymer from the first end to the second end, the passage having a distal end and a proximal end, wherein the proximal end of the passage is offset from the axis by an angle $\alpha$, where $\alpha > 5°$, the deformable plug having a frustoconical proximal portion.

In another aspect of the present invention, a method includes applying a nasal plug having an outer tube and an inner tube within a lumen of the outer tube, the inner tube having a flexible movable wall; upon inhalation of the patient, air flow causing the flexible movable wall to move within the lumen of the outer tube to block air flow through at least a part of the outer tube and directing substantially all air flow into a lumen of the inner tube to exit at a predetermined location with the patient's nasal cavity; and upon exhalation of the patient, air flow causing the flexible movable wall to move wall within the lumen of the outer tube to cause air flow to pass through both the lumen of the inner tube and the lumen of the outer tube.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Further embodiments, features, and advantages of the nasal plug, as well as the structure and operation of the various embodiments of the nasal plug, are described in detail below with reference to the accompanying drawings.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

FIG. 4A is a top view of an embodiment nasal plug according to principles described herein.

FIG. 4B is a bottom view of the example nasal plug of FIG. 4A.

FIG. 4C is a front view of the example nasal plug of FIG. 4A.

FIG. 4D is a cross-sectional side view of the example nasal plug of FIG. 4A taken along line A-A of FIG. 4C.

DESCRIPTION OF THE EXEMPLARY EMBODIMENTS

The present invention may be understood more readily by reference to the following detailed description of example embodiments of the invention and to the Figures and their previous and following description.

As used in the specification and the appended claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Reference will now be made in detail to embodiments of the nasal plug with reference to the accompanying figures. Wherever possible, the same reference numbers are used throughout the drawings to refer to the same or like parts.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The mechanisms leading to perception of nasal obstruction by patients with nasal sinus disease remain poorly understood. Subjective complaints often bear little relationship to the actual physical resistance to airflow in the nose. Altered nasal aerodynamics is often suspected as a major contributing factor. Our study has shown that, as an extreme example, for all ENS patients that were seen in our clinic, previous surgeries that opened up the nasal airway, resulted paradoxically in nasal airflow forming into a narrow jet towards the middle meatus region, leaving the other airway with significantly reduced airflow. The over-congregated nasal airflow may over stress a small patch of the nasal mucosa resulting in excessive nasal dryness or crusting of which many ENS patients complained. It will also reduce the capacity of the nasal mucosal to detect airflow.

Figure 1:
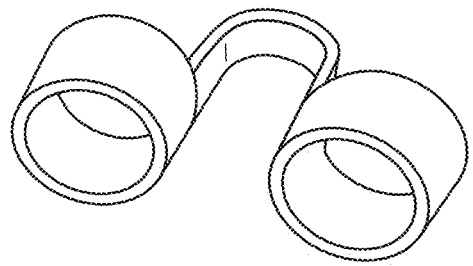
FIG. 1 illustrates a related art nasal dilator.
Figure 2:
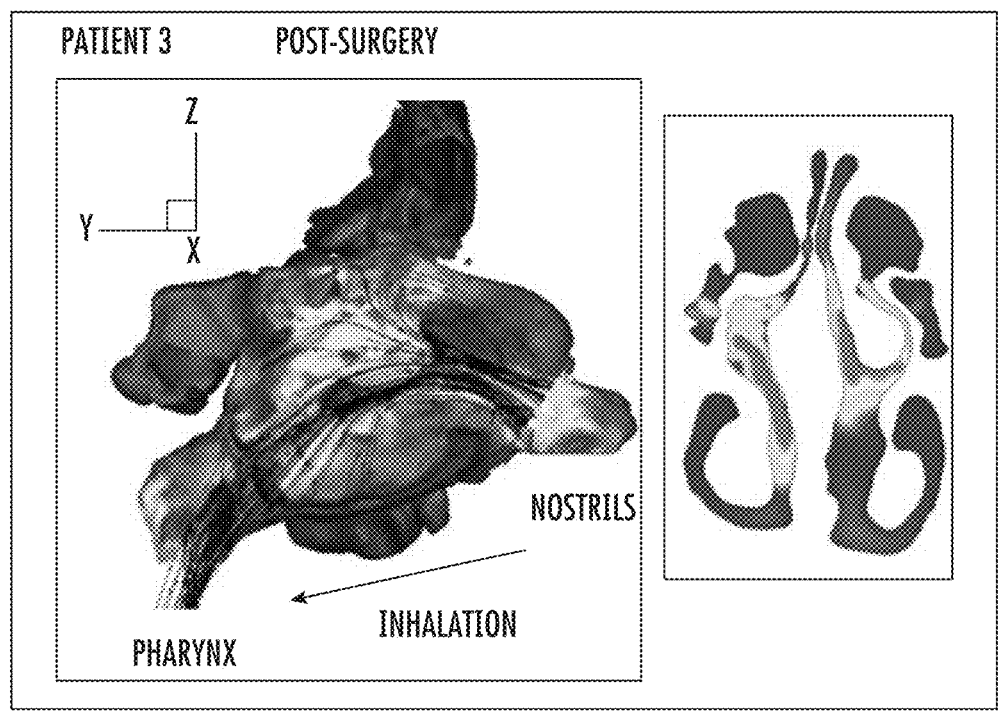
FIG. 2 illustrates nasal air flow in a patient's sinus cavity.

Referring to FIG. 2, according to principles of the present invention, the nasal flow in the patient is directed away from the red (high flow) zone and into the blue (low flow) zone to potentially alleviate patient's symptoms.

Accordingly, described herein is a deformable nasal plug with various features to provide a narrow jet of inhaled air directed toward a portion of a wall of the patients nasal cavity, and, in some embodiments, a vent to increase the flow rate of air exhaled by the patient. Embodiments of the nasal plug described herein comprises material that is deformable to allow the plug to be accepted into and fluidically seal a patient's nasal nares. In aspects described herein, in addition to redirecting incoming airflow to therapeutic zones in the nasal mucosa, embodiments described herein maintain the functionality of dilating the frontal nasal valve. As a result, obstructions that stem from structural complications beyond the nasal valve can be addressed by redirecting incoming airflow to therapeutic zones in the nasal mucosa while also maintaining the functionality of dilating the frontal nasal valve. Therefore, this technology has the potential to provide symptom relief to a wider range of nasal obstruction patients.

Figure 3A:
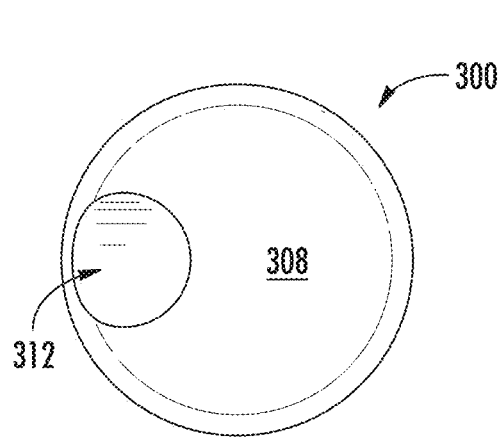
FIG. 3A is a top view of an embodiment of a nasal plug according to principles described herein.
Figure 3B:
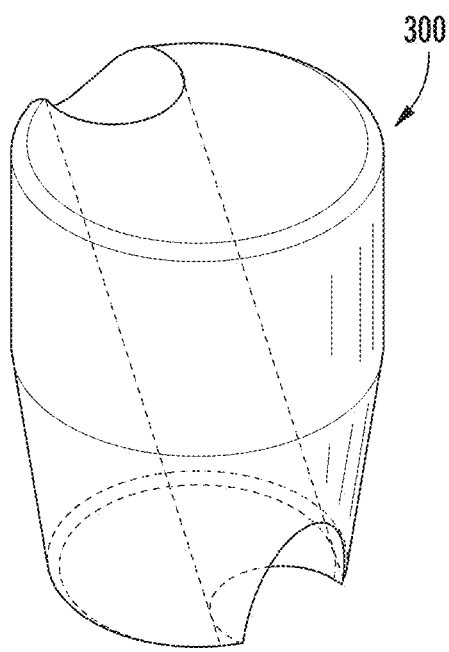
FIG. 3B is a perspective line drawing of the example nasal plug of FIG. 3A.
Figure 3C:
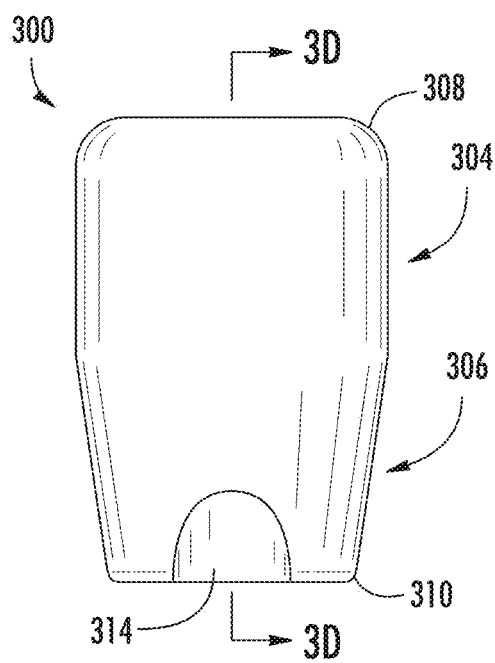
FIG. 3C is a front view of the example nasal plug of FIG. 3A.
Figure 3D:
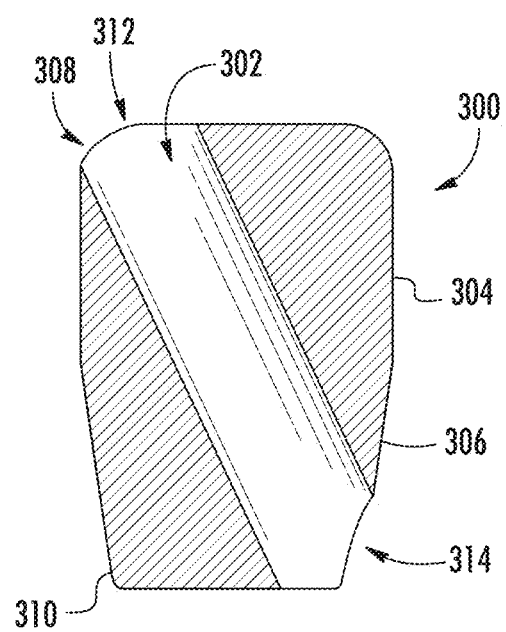
FIG. 3D is a cross-sectional side view of the example nasal plug of FIG. 3A taken along line A-A of FIG. 3C.

FIG. 3A is a top view of an embodiment of a nasal plug according to principles described herein. FIG. 3B is a perspective line drawing of the example nasal plug of FIG. 3A. FIG. 3C is a front view of the example nasal plug of FIG. 3A. FIG. 3D is a cross-sectional side view of the example nasal plug of FIG. 3A taken along line A-A of FIG. 3C.

To address symptoms experienced by various patients described herein, the inventor have proposed a nasal plug 300 with a channel 302 passing therethrough to direct inhaled gasses at an angle with respect to the patients nasal wall. The actual profile of the nasal plug could be of any shape sufficient to block air flow between a surface of the nasal plug and a patient's nostril/nares inner surface, and such profile may be dependent on the pliability of the nasal plug material. For example, if the nasal plug is made of a deformable material, as illustrated in FIGS. 3A-3D. The profile may be substantially cylindrical, but could also be angular, e.g., rectangular, square, triangular or could be oval, spherical, or other shape suitable to block air passage through the nostril but for a passage according to principles of the present invention. As illustrated in FIGS. 3A-3D, the exemplary nasal plug has a cylindrical base 304 and a frustoconical upper portion 306 for insertion into the nostril/nares of a patient. The nasal plug may be made of foam, silicon, or any other soft material. In an aspect, the designs herein lend themselves to three dimensional (3D) printing as a method of manufacturing, although other techniques such as injection molding and the like may be used to make the nasal plugs described herein. That is, the nasal plug may be made of printable polymer, silicon, resin or plastic or any deformable polymer or plastic material appropriate for known molding techniques. In a manufacturing aspect, the channel 302 may be formed with the formation of the nasal plug 308, e.g., as a void during 3D printing or molding or may be formed by boring a hole/channel through a previously-formed nasal plug body.

As can be seen in FIG. 3D, the channel 302 extends from through the nasal plug from a distal end 308 of the plug to a proximal end 310 of the plug, where distal is used herein to be the portion of the plug that is external to a person once the plug is inserted into the person's nostril. The channel 302 may be formed as a via through the nasal plug 300 such that no tube or other support structure is required. In another aspect, a tube or support structure (not shown) may be provided within the channel 302 to provide additional stability and to maintain the passage or bore through the nasal plug 300. Such support structure can be integral or fixedly attached to the interior of the nasal plug passage/channel 302 or may be held in place by other methods, such as interference fit or friction fit, or may even be held in place by an adhesive. The tubes may be made of plastic or any material that can maintain the shape and structure. Although illustrated as cylindrical, the tube may be of any shape that provides appropriate airflow through the passage, such as conical or squares.

As illustrated in FIGS. 3A-3D, an embodiment of the nasal plug according to principles of the present application includes parts: a nasal plug of pliable or deformable material having a passage/channel 302 there through. In practice, a nasal plug of this configuration may be applied to each nostril (nostril) of a patient. As illustrated in FIG. 3D, the channel 302 has a predetermined angle with respect to an axial direction of the nasal plug to provide airflow to the nostril at a predetermined location within the sinuses.

While shown as a passage with a fixed angle from distal to proximal end of the nasal plug, such is not required. For example, a portion of the passage may be angled to provide an exit at the proximal end of the nasal plug at the appropriate predetermined angle. The nasal plug 308 may be moved or rotated within the patient's nostril to direct air flow through the channel 302 to an appropriate location, e.g., a location where the patient finds relief of his symptoms. In addition, the angled nature of the nasal plug will also allow the user to modify the angle of airflow redirection by decreasing or increasing the angle by the degree of insertion of the plug. For example, the further the plug is placed into the nasal cavity, the greater the redirection angle. The predetermined angle may be different or the same for different nostrils in the same patient. For example, the angle may be >20° from a central axis (axial direction) of the nasal plug. The angle may range from about 5° to 90°. At least in some circumstances, the angle should be determined such that the air flow through the passage is directed to a person's lower meatus. That is, the angle of the passage may be in the range of >5°, and in some circumstances, >10°.

Figure 3E:
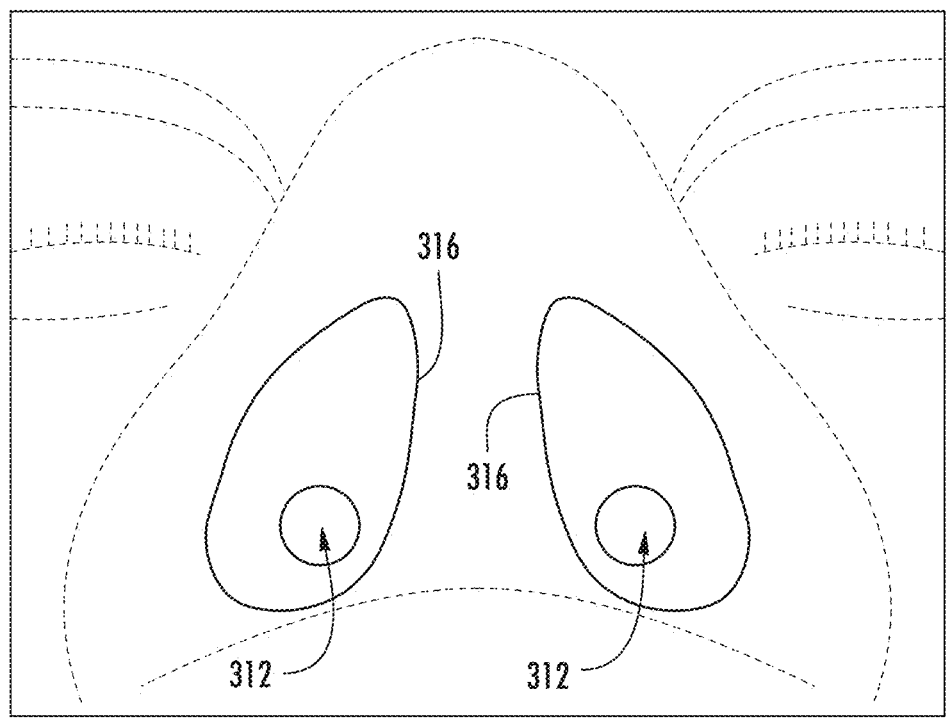
FIG. 3E illustrates an example, but not limiting, placement of the nasal plug channels in the nostrils of a patient looking upward into the patient's nostrils.

FIG. 3E illustrates an example, but not limiting, placement of the nasal plug channels in the nostrils of a patient looking upward into the patient's nostrils 316. The placement of the channels illustrated is merely an example, and the location of the channels distal outlets 312 with respect the nostrils may vary depending on the channel's path, e.g. a straight diagonal from distal to proximal end or a bent path, where the angle occurs spaced from the distal end.

While the embodiment illustrated in FIGS. 3A-3D provides a device to obstruct/occlude airflow into a patient's nasal cavity and to concentrate this airflow into a small channel, in some circumstances, improved exhalation air flow may be desired. Accordingly, in another embodiment according to principles described herein, a one way channel may be provided to restrict airflow coming in and to allow airflow going out.

FIG. 4A is a top view of an embodiment of a vented nasal plug according to principles described herein. FIG. 4B is a bottom view of the example nasal plug of FIG. 4A. FIG. 4C is a front view of the example nasal plug of FIG. 4A. FIG. 4D is a cross-sectional side view of the example nasal plug of FIG. 4A taken along line A-A of FIG. 4C.

FIGS. 4A-4D illustrate a nasal plug 400 with a channel for directing inhaled air flow into a small channel (toward a patient's nasal cavity wall) with a valve for allowing greater exhalation flow out, e.g., via the channel 402 and via an ancillary channel 418. As demonstrated in FIGS. 4A-4D, the nasal plug 400 includes a small curved or angled hollow tube 420 with similar inner diameter as the nasal plug in FIGS. 3A-3D where the small curved hollow tube 420 and its inner diameter provide a channel 402 for causing inflow/inhaled gas to be directed to the patient's nasal cavity wall, functioning similarly to the channel 302 of FIGS. 3A-3D. The small curved or angled tube 420 is within the lumen of a larger hollow tube 422, which may be curved, angled or substantially straight. The inner smaller tube 420 is not coextensive with the larger outer tube, such that a wall 430 of the inner smaller tube 420 has a free end 430a within the lumen larger tube 422, the free end 430a being movable upon application of pressure, such as when air is inhaled. That is, the free end 430a forms a passive valve in cooperation with the inner surface of the wall of the larger outer tube 422.

The outer size and shape of the larger hollow tube 422 has a diameter sized appropriately to be received in a patient's nostril and block airflow around the nasal plug 400 (i.e., between the outer surface of the larger hollow tube and the inner wall of the patient's nostril. The larger hollow tube may have a similar size/shape of the nasal plug of FIGS. 3A-3E or may be curved as shown in FIGS. 4A-4D. In an aspect, each of the small curved hollow tube 420 and the larger curved hollow tube 422 have proximal outlets 424 and 426 that are oriented at an angle with respect to a plane of a distal outlet 428 of the larger hollow tube 422. As illustrated in FIG. 4D, an axial direction of the inner tube proximal outlet 424 may be at an angle β with respect to a direction perpendicular to the plane of the proximal outlet 426 of the larger hollow tube 420. An outer wall 430 of the small hollow tube 420 may have at least a portion an angle β with respect to a direction perpendicular to the plane of the distal outlet 428 of the larger hollow tube 420. A difference between the angle α and the angle β creates a narrow opening on the inhalation side, while providing a wider opening on the exhalation side. This will allow most of the airflow to follow the path of least resistance during inhalation through the smaller but more open inner tube, but will then allow for air to vent out through inner tube and a gap between the outer and inner tube.

Although shown in FIGS. 4A-4D as a curved plug, such is not necessary. curvature both channels in the design as shown in FIGS. 4A-4D allows for a greater redirection angle. In the design in FIGS. 4A-4D, a redirection angle of 0°-90° (α+β) for inhaled air is possible if the nasal aid is inserted fully into the nostril. For example, as shown in FIG. 4D, α=30° and β=45°. An example angle of redirection of approximately 75° is illustrated in FIGS. 4A-4D.

In an aspect, angle may be >20° from a central axis (axial direction) of the nasal plug. The angle may range from about 5° to 90°. At least in some circumstances, the angle should be determined such that the air flow through the passage is directed to a person's lower meatus. That is, the angle of the passage may be in the range of >5°, and in some circumstances, >10°.

In addition, the curved or angled nature of the nasal plug will also allow the user to modify the angle of airflow redirection by decreasing or increasing the angle by the degree of insertion of the plug. For example, the further the plug is placed into the nasal cavity, the greater the redirection angle. With this design, the thickness and the angle of curvature or deflection for the inner and outer tubes, along with the position of the inner channel, can be modified to increase or decrease the maximum possible airflow redirection angle as well as modify the degree of constriction of airflow.

Upon inhalation, the free end 430a of the wall 430 is moved by pressure created by the patient's inhalation to close the vent area 418 by moving the free end 430a to abut the inner wall surface of the larger outer tube 422 within the lumen, thus forcing the inhaled air into the channel 402 of the smaller tube 420. Upon exhalation, the free end 430a is forced away from the inner wall surface of the larger outer tube by pressure created by the patient's exhalation such that the vent 418 is opened, allowing exhaled air to pass through both proximal outlets 424 and 426 and into channel 402 and the vent 418, respectively, and into the lumen of the larger tube to the distal outlet 428. Thus, the free end forms a passive valve with the lumen of the larger tube. In addition to the redirecting airflow to therapeutic zones in the nasal mucosa, the nasal plug illustrated in FIGS. 4A-4E serves to maintain the functionality of dilating the frontal nasal valve.

The actual profile of the nasal plug could be of any shape sufficient to block air flow between a surface of the nasal plug and a patient's nostril/nares inner surface, and such profile may be dependent on the pliability of the nasal plug material. The cross-sectional profile may be substantially circular, but could also be angular, e.g., rectangular, square, triangular or could be oval, spherical, or other shape suitable to block air passage through the nostril but for a passage according to principles of the present invention.

Figure 9:
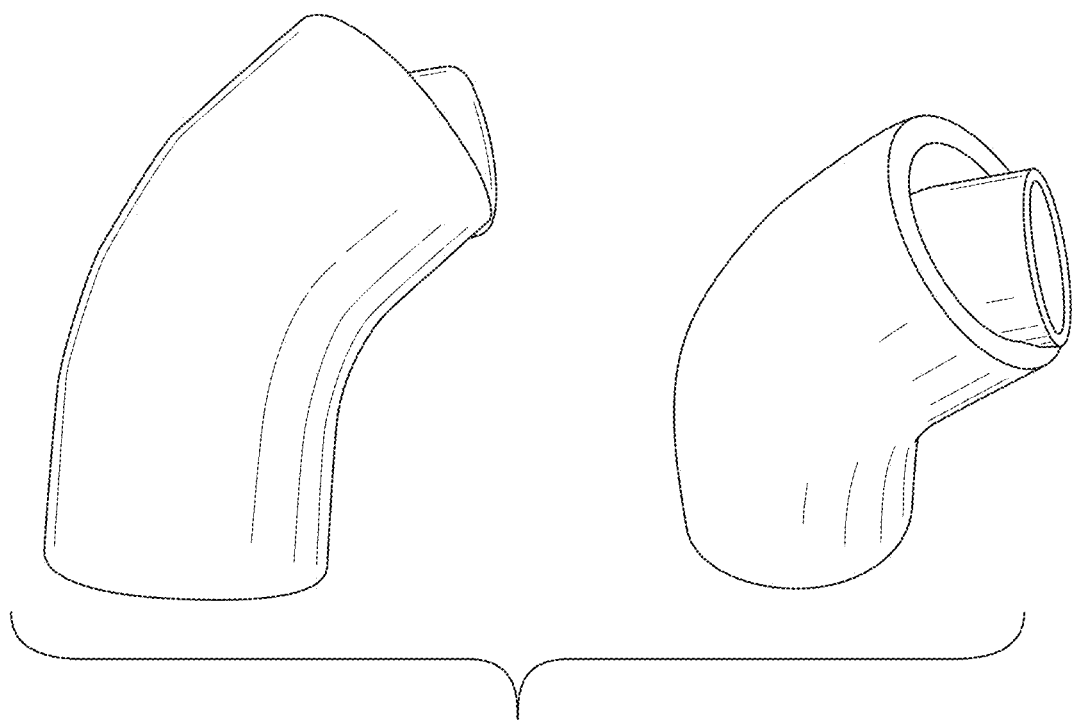
FIG. 9 is a photograph showing the example embodiment of FIGS. 4A-4D manufactured using stereolithography (SLA) printing techniques.

FIG. 9 is a photograph showing the example embodiment of FIGS. 4A-4D manufactured using stereolithography (SLA) printing techniques.

Figure 5A:
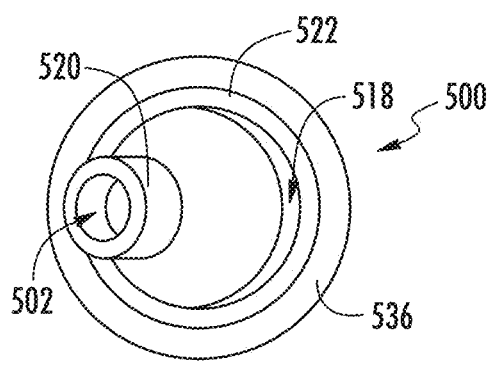
FIG. 5A is a top view of another embodiment nasal plug according to principles described herein.
Figure 5B:
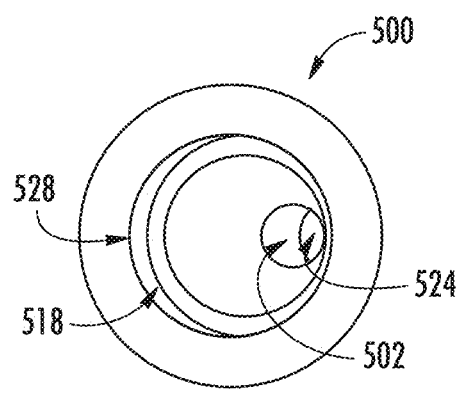
FIG. 5B is a bottom view of the example nasal plug of FIG. 5A.
Figure 5C:
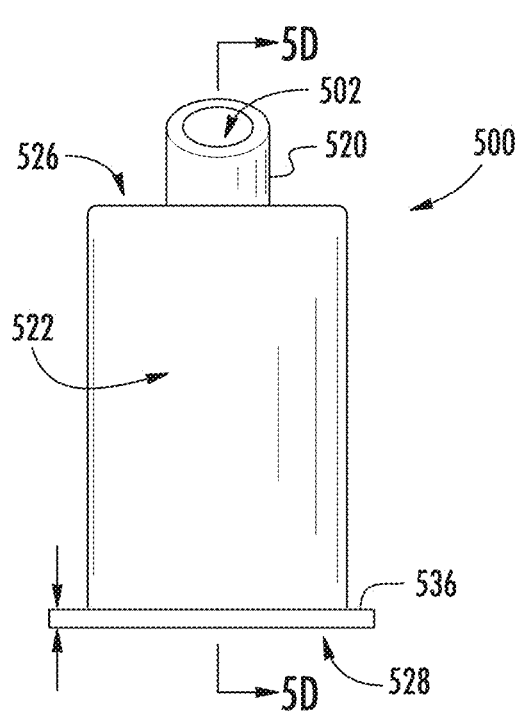
FIG. 5C is a front view of the example nasal plug of FIG. 5A.
Figure 5D:
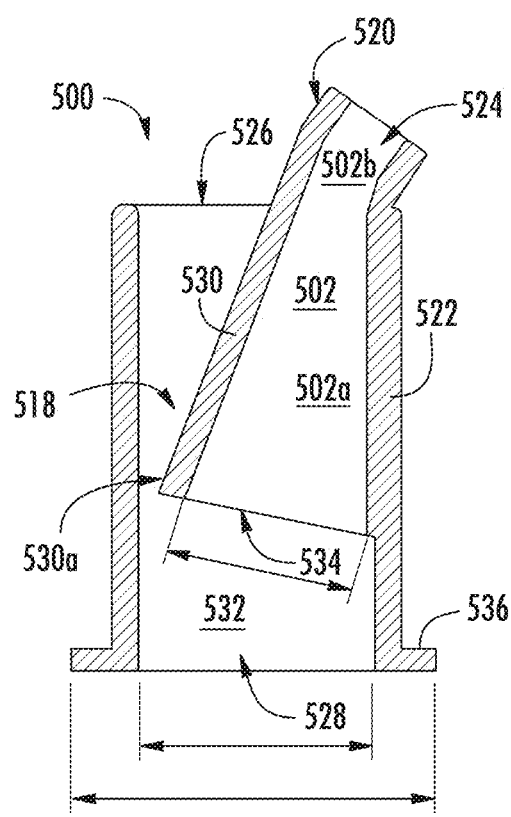
FIG. 5D is a cross-sectional side view of the example nasal plug of FIG. 4A taken along line A-A of FIG. 5C.

FIGS. 5A-5D illustrates another embodiment of the vented nasal plug according to principles described herein. Referring to FIGS. 5A, 5B and 5C, a vented nasal plug 500 includes a passive one way valve. As demonstrated in FIG. 5D, in lieu of a uniform curved inner channel 402 of the embodiment of FIGS. 4A-4D, a cone-like/funnel shaped inner channel 502 captures a larger degree of airflow over the embodiment of FIGS. 4A-D, thereby providing an easier path for the incoming airflow to follow, while maintaining the narrow opening (proximal outlet 524) on the inhalation side (funnel side) of the device. The cone-like inner channel 502 also provides a larger vent opening 518 on the exhalation side (vent side) of the device than the prior described embodiment, allowing a larger amount of airflow to escape out the vent opening. The proximal outlet 524 at the end of the cone-like inner channel may be narrowed in comparison to the uniform channel of FIGS. 3A-3D in order to facilitate a higher exit velocity and increase the stimulation of the air jet.

As shown in FIGS. 5A-5D, the funnel shaped channel 502 includes a cone-shaped/frustoconical portion 502a with a wall 530 extending into a larger cylindrical lumen 532 formed by a wall of a larger tube 522. The funnel shaped channel further comprises a tubular channel 502b adjacent to and in fluid communication with the frustoconical portion 502a. The tubular portion 502b may connect with the cone-shaped portion seamlessly to form a continuous lumen between a distal opening 534 of the conical portion and a proximal outlet 524 of the tubular portion, wherein the tubular portion is angled with respect to a direction perpendicular to the plane of the distal outlet 528 of the larger tube 522. the proximal outlet 524 of the tubular portion 502b of the funnel shaped channel 502 may extend beyond the end proximal outlet 526 of the larger tube 522. While shown as extending beyond the proximal outlet/end of the larger tube 522, the proximal outlet 524 of the tubular portion 502b of the funnel shaped channel 522 does not need to extend beyond the end proximal outlet 526 of the larger tube 522 so long as the proximal outlet 524 causes inhaled gas to flow in a direction at an angle with respect to the plane of the proximal outlet 526 of the outer larger tube 522. In the illustrated embodiment, the wall 530 forms an angle of about 75° at rest with respect to the inner surface of the wall of the larger tube 522 on the inhalation side of the tube. At least part of the outer structure of the funnel-shaped portion may be formed by the wall of outer tube 522. The angle may range from 10°-90° without departing from the spirit and scope of the invention.

The wall 530 may flex with respect to the tubular portion 502b of the funnel shaped channel 502. For example, the wall 530 may be made of a thin layer of flexible material such as silicon, which may be formed of the same material as the remainder of the vented nasal plug 500. The wall 530 being movable includes a free end 530a within the lumen of the outer larger tube 522. In operation, upon inhalation, the free end 530a of the wall 530 is moved by pressure created by the patient's inhalation of air thus closing close the vent area 518 by moving the free end 530a to abut the inner wall surface of the larger outer tube 522 within the lumen, thus forcing the inhaled air into the channel 502 of the smaller tube 520. Upon exhalation, the free end 530a is forced away from the inner wall surface of the larger outer tube by pressure created by patient exhalation such that the vent 518 is opened, allowing exhaled air to pass through both proximal outlets 524 and 526 and into channel 502 and the vent 518, respectively, and into the lumen of the larger tube to the distal outlet 528. Thus, the wall 530 and its free end 530a form a passive valve with the lumen of the larger tube.

Also illustrated in FIGS. 5A-5D is an optional lip 536 at the inhalation opening/distal outlet 528 of the nasal plug 500. The lip 536 reduces the risk of accidental aspiration of the nasal plug 500 during use. The lip is configured to "catch" on the opening of the nostrils and also provide an easier grip for the user to manipulate the device.

Similar to the prior designs, the thickness of the tube walls and the angle of the inner cone/curved head can be manipulated to modify the vent opening and the angle of airflow redirection. In the design in FIGS. 5A-5D, a redirection angle of 0°-90° for inhaled air is possible if the nasal aid is inserted fully into the nostril. An example angle of redirection of approximately 45° is illustrated in FIGS. 5A-5D. The angle may be different or the same for different nostrils in the same patient. For example, the angle may be >20° from a central axis (axial direction) of the nasal plug. The angle may range from about 5° to 90°. At least in some circumstances, the angle should be determined such that the air flow through the passage is directed to a person's lower meatus. That is, the angle of the passage may be in the range of >5°, and in some circumstances, >10°. In addition to the redirecting airflow to therapeutic zones in the nasal mucosa, the nasal plug illustrated in FIGS. 5A-5E serves to maintain the functionality of dilating the frontal nasal valve.

Figure 10:
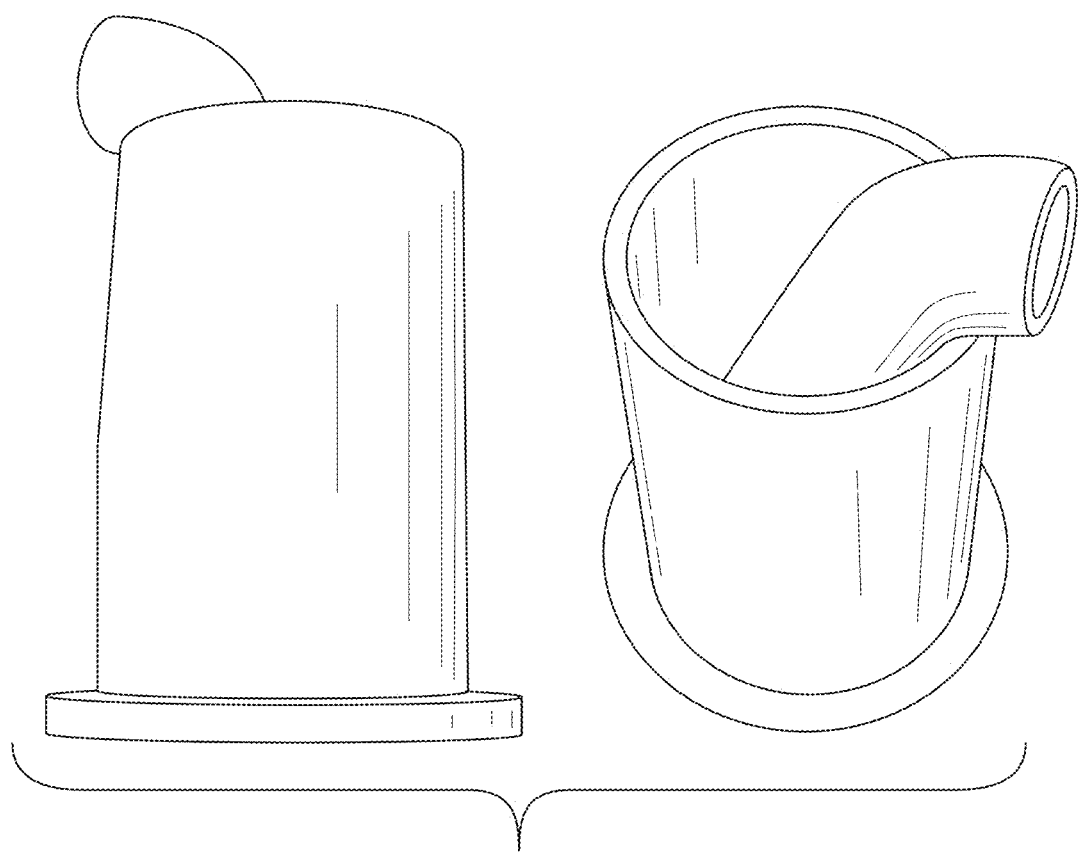
FIG. 10 is a photograph showing a sample nasal plug as shown in FIGS. 5A-5D manufactured according to SLA printing techniques.

FIG. 10 is a photograph showing a sample nasal plug as shown in FIGS. 5A-5D manufactured according to SLA printing techniques.

Figure 6A:
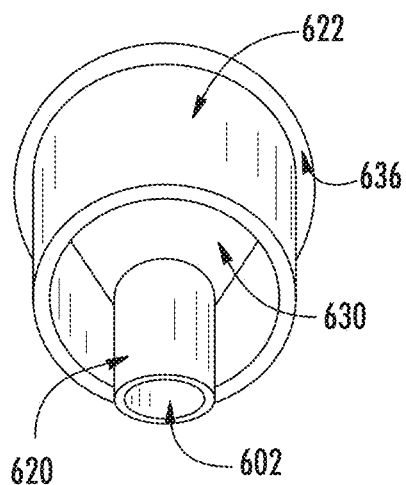
FIG. 6A is a perspective top view of another example nasal plug according to principles described herein.
Figure 6B:
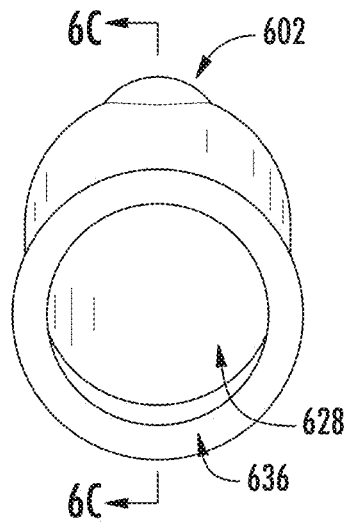
FIG. 6B is a bottom view of the example nasal plug of FIG. 6A.
Figure 6C:
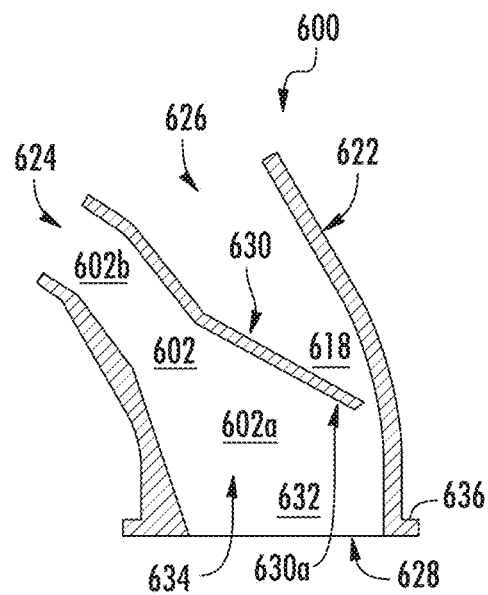
FIG. 6C is a cross-sectional side view of the example nasal plug of FIG. 6A, taken along line A-A of FIG. 6B.
Figure 6D:
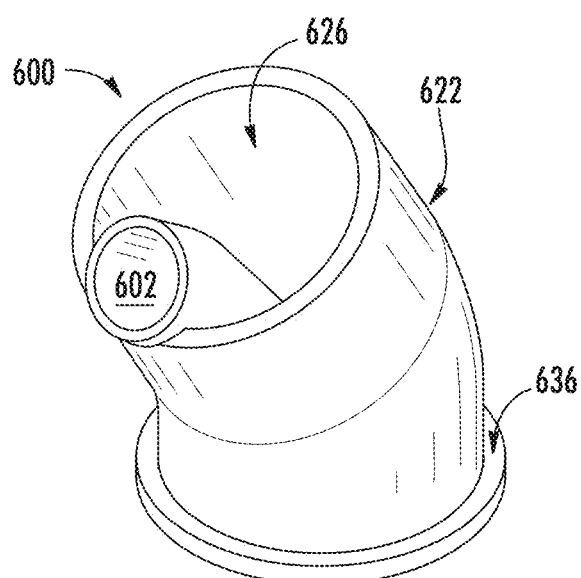
FIG. 6D is a perspective view of the nasal plug of FIGS. 6A-C.

FIG. 6A is a perspective top view of another example nasal plug according to principles described herein. FIG. 6B is a bottom view of the example nasal plug of FIG. 6A. FIG. 6C is a cross-sectional side view of the example nasal plug of FIG. 6A, taken along line A-A of FIG. 6B.

Like the embodiment shown in FIGS. 5A-5D, the example vented nasal plug of FIGS. 6A-6D includes a cone-like/funnel shaped inner channel 602 captures a larger degree of airflow over the embodiment of FIGS. 4A-D, thereby providing an easier path for the incoming airflow to follow, while maintaining the narrow opening (proximal outlet 624) on the inhalation side (funnel side) of the device. The cone-like inner channel 602 also provides a larger vent opening 618 on the exhalation side (vent side) of the device than the prior described embodiment, allowing a larger amount of airflow to escape out the vent opening. The proximal outlet 624 at the end of the cone-like inner channel may be narrowed in comparison to the uniform channel of FIGS. 3A-3D in order to facilitate a higher exit velocity and increase the stimulation of the air jet.

As shown in FIGS. 6A-6D, the funnel shaped channel 602 includes a cone-shaped/frustoconical portion 602a with a wall 630 extending into a larger lumen 632 formed by a wall of a larger tube 622. Unlike the embodiment of FIGS. 5A-5D, the outer larger tube 622 is a "curved cylinder" or an "arched tube". The funnel shaped channel 602 further comprises a tubular channel 602b adjacent to and in fluid communication with the frustoconical portion 602a. The tubular portion 602b may connect with the cone-shaped portion seamlessly to form a continuous lumen between a distal opening 634 of the conical portion and a proximal outlet 624 of the tubular portion, wherein the tubular portion is angled with respect to or curved away from a direction perpendicular to the plane of the distal outlet 628 of the larger tube 622. the proximal outlet 624 of the tubular portion 602b of the funnel shaped channel 622 may extend beyond the end proximal outlet 626 of the larger tube 622. While shown as extending beyond the proximal outlet/end of the larger tube 622, the proximal outlet 624 of the tubular portion 602b of the funnel shaped channel 622 does not need to extend beyond the end proximal outlet 626 of the larger tube 622 so long as the proximal outlet 624 causes inhaled gas to flow in a direction at an angle with respect to the plane of the proximal outlet 626 of the outer larger tube 622. In the illustrated embodiment, the wall 630 forms an angle of about 75° at rest with respect to the inner surface of the wall of the larger tube 622 on the inhalation side of the tube. The angle may range from 10°-90° without departing from the spirit and scope of the invention. At least part of the outer structure of the funnel-shaped portion may be formed by the wall of outer tube 622.

The wall 630 may flex with respect to the tubular portion 602b of the funnel shaped channel 602. For example, the wall 630 may be made of a thin layer of flexible material such as silicon, which may be formed of the same material as the remainder of the vented nasal plug 600. The wall 630 being movable includes a free end 630a within the lumen of the outer larger tube 622. In operation, upon inhalation, the free end 630a of the wall 630 is moved by pressure created by the patient's inhalation of air thus closing close the vent area 618 by moving the free end 630a to abut the inner wall surface of the larger outer tube 622 within the lumen, thus forcing the inhaled air into the channel 602 of the smaller tube 620. Upon exhalation, the free end 630a is forced away from the inner wall surface of the larger outer tube by pressure created by patient exhalation such that the vent 618 is opened, allowing exhaled air to pass through both proximal outlets 624 and 626 and into channel 602 and the vent 618, respectively, and into the lumen of the larger tube to the distal outlet 628. Thus, the wall 630 and its free end 630a form a passive valve with the lumen of the larger tube.

Also illustrated in FIGS. 6A-6D is an optional lip 636 at the inhalation opening/distal outlet 628 of the nasal plug 600. The lip 636 reduces the risk of accidental aspiration of the nasal plug 600 during use. The lip is configured to "catch" on the opening of the nostrils and also provide an easier grip for the user to manipulate the device.

Similar to the prior designs, the thickness of the tube walls and the angle of the inner cone/curved head can be manipulated to modify the vent opening and the angle of airflow redirection. In the design in FIGS. 6A-6D, a redirection angle of 0°-90° for inhaled air is possible if the nasal aid is inserted fully into the nostril. An example angle of redirection of approximately 45° is illustrated in FIGS. 6A-6D.

The angle may be different or the same for different nostrils in the same patient. For example, the angle may be >20° from a central axis (axial direction) of the nasal plug. The angle may range from about 5° to 90°. At least in some circumstances, the angle should be determined such that the air flow through the passage is directed to a person's lower meatus. That is, the angle of the passage may be in the range of >5°, and in some circumstances, >10°. In addition to the redirecting airflow to therapeutic zones in the nasal mucosa, the nasal plug illustrated in FIGS. 6A-6E serves to maintain the functionality of dilating the frontal nasal valve.

In the embodiment of FIGS. 6A-6D, the funnel portion 602a distal opening 634 has at least a portion of its periphery substantially co-incident with the distal outlet 628. The lumen of the outer tube may be wider than the lumen of the outer tube described below with respect to FIGS. 7A-7D and FIGS. 8A-8D. This configuration has advantages for patients with larger nostrils/nares.

Figure 7A:
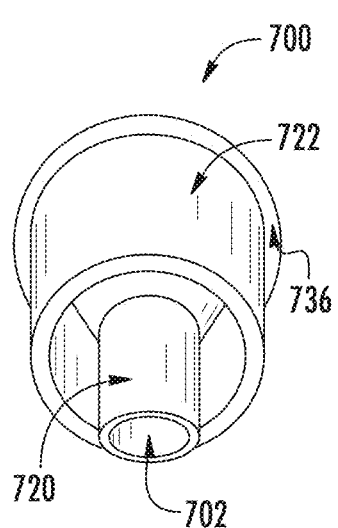
FIG. 7A is a perspective top view of another example nasal plug according to principles described herein.
Figure 7B:
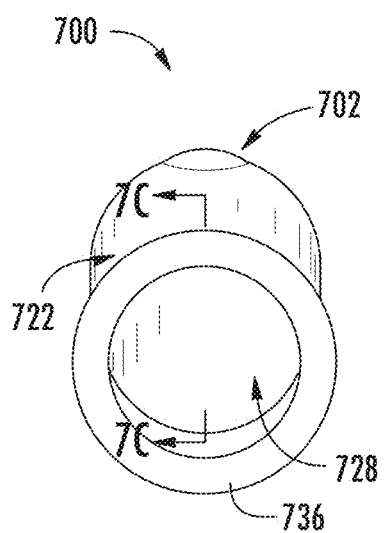
FIG. 7B is a bottom view of the example nasal plug of FIG. 7A.
Figure 7C:
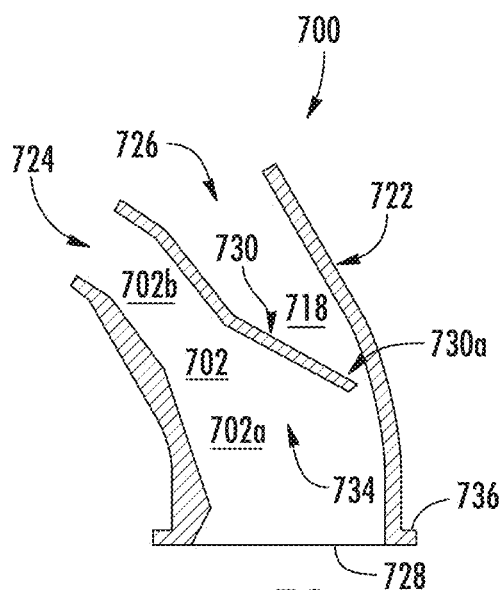
FIG. 7C is a cross-sectional side view of the example nasal plug of FIG. 7A, taken along line A-A of FIG. 7B.
Figure 7D:
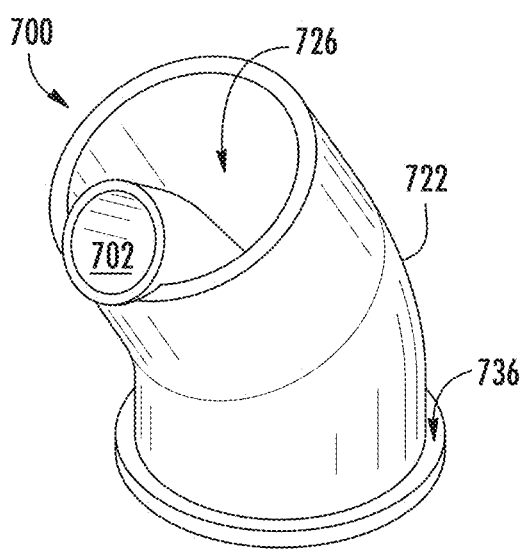
FIG. 7D is a perspective view of the nasal plug of FIGS. 7A-C.

FIG. 7A is a perspective top view of another example nasal plug according to principles described herein. FIG. 7B is a bottom view of the example nasal plug of FIG. 7A. FIG. 7C is a cross-sectional side view of the example nasal plug of FIG. 7A, taken along line A-A of FIG. 7B. FIG. 7D is a perspective view of the nasal plug of FIGS. 7A-C.

The embodiment of the vented nasal plug illustrated in FIGS. 7A-7D includes a cone-like/funnel shaped inner channel 702 captures a larger degree of airflow over the embodiment of FIGS. 4A-D, thereby providing an easier path for the incoming airflow to follow, while maintaining the narrow opening (proximal outlet 724) on the inhalation side (funnel side) of the device. The cone-like inner channel 702 also provides a larger vent opening 718 on the exhalation side (vent side) of the device than the prior described embodiment, allowing a larger amount of airflow to escape out the vent opening. The proximal outlet 724 at the end of the cone-like inner channel may be narrowed in comparison to the uniform channel of FIGS. 3A-3D in order to facilitate a higher exit velocity and increase the stimulation of the air jet.

As shown in FIGS. 7A-7D, the funnel shaped channel 702 includes a cone-shaped/frustoconical portion 702a with a wall 730 extending into a larger lumen 732 formed by a wall of a larger tube 722. Unlike the embodiment of FIGS. 5A-5D, the outer larger tube 722 is a "curved cylinder" or an "arched tube". The funnel shaped channel 702 further comprises a tubular channel 702b adjacent to and in fluid communication with the frustoconical portion 702a. The tubular portion 702b may connect with the cone-shaped portion seamlessly to form a continuous lumen between a distal opening 734 of the conical portion and a proximal outlet 724 of the tubular portion, wherein the tubular portion is angled with respect to or curved away from a direction perpendicular to the plane of the distal outlet 728 of the larger tube 720. the proximal outlet 724 of the tubular portion 702b of the funnel shaped channel 722 may extend beyond the end proximal outlet 726 of the larger tube 722. While shown as extending beyond the proximal outlet/end of the larger tube 722, the proximal outlet 724 of the tubular portion 702b of the funnel shaped channel 722 does not need to extend beyond the end proximal outlet 726 of the larger tube 722 so long as the proximal outlet 724 causes inhaled gas to flow in a direction at an angle with respect to the plane of the proximal outlet 726 of the outer larger tube 722. In the illustrated embodiment, the wall 730 forms an angle of about 75° at rest with respect to the inner surface of the wall of the larger tube 722 on the inhalation side of the tube. The angle may range from 10°-90° without departing from the spirit and scope of the invention. At least part of the outer structure of the funnel-shaped portion may be formed by the wall of outer tube 722.

The wall 730 may flex with respect to the tubular portion 702b of the funnel shaped channel 702. For example, the wall 730 may be made of a thin layer of flexible material such as silicon, which may be formed of the same material as the remainder of the vented nasal plug 700. The wall 730 being movable includes a free end 730a within the lumen of the outer larger tube 722. In operation, upon inhalation, the free end 730a of the wall 730 is moved by pressure created by the patient's inhalation of air thus closing close the vent area 718 by moving the free end 730a to abut the inner wall surface of the larger outer tube 722 within the lumen, thus forcing the inhaled air into the channel 702 of the smaller tube 720. Upon exhalation, the free end 730a is forced away from the inner wall surface of the larger outer tube by pressure created by patient exhalation such that the vent 718 is opened, allowing exhaled air to pass through both proximal outlets 724 and 726 and into channel 702 and the vent 718, respectively, and into the lumen of the larger tube to the distal outlet 728. Thus, the wall 730 and its free end 730a form a passive valve with the lumen of the larger tube.

Also illustrated in FIGS. 7A-7D is an optional lip 736 at the inhalation opening/distal outlet 728 of the nasal plug 700. The lip 736 reduces the risk of accidental aspiration of the nasal plug 700 during use. The lip is configured to "catch" on the opening of the nostrils and also provide an easier grip for the user to manipulate the device.

Similar to the prior designs, the thickness of the tube walls and the angle of the inner cone/curved head can be manipulated to modify the vent opening and the angle of airflow redirection. In the design in FIGS. 7A-7D, a redirection angle of 0°-90° for inhaled air is possible if the nasal aid is inserted fully into the nostril. An example angle of redirection of approximately 45° is illustrated in FIGS. 7A-7D.

In the embodiment of FIGS. 7A-7D, the funnel portion 702a distal opening 734 has periphery spaced that may be spaced away from the distal outlet 728. The lumen of the outer tube 722 may be narrower than the lumen of the embodiments of FIGS. 6A-6D, but wider than the lumen of the outer tube described below with respect to FIGS. 8A-8D. This configuration has advantages for patients with standard-sized nostrils/nares.

The angle may be different or the same for different nostrils in the same patient. For example, the angle may be >20° from a central axis (axial direction) of the nasal plug. The angle may range from about 5° to 90°. At least in some circumstances, the angle should be determined such that the air flow through the passage is directed to a person's lower meatus. That is, the angle of the passage may be in the range of >5°, and in some circumstances, >10°. In addition to the redirecting airflow to therapeutic zones in the nasal mucosa, the nasal plug illustrated in FIGS. 7A-7E serves to maintain the functionality of dilating the frontal nasal valve.

Figure 11:
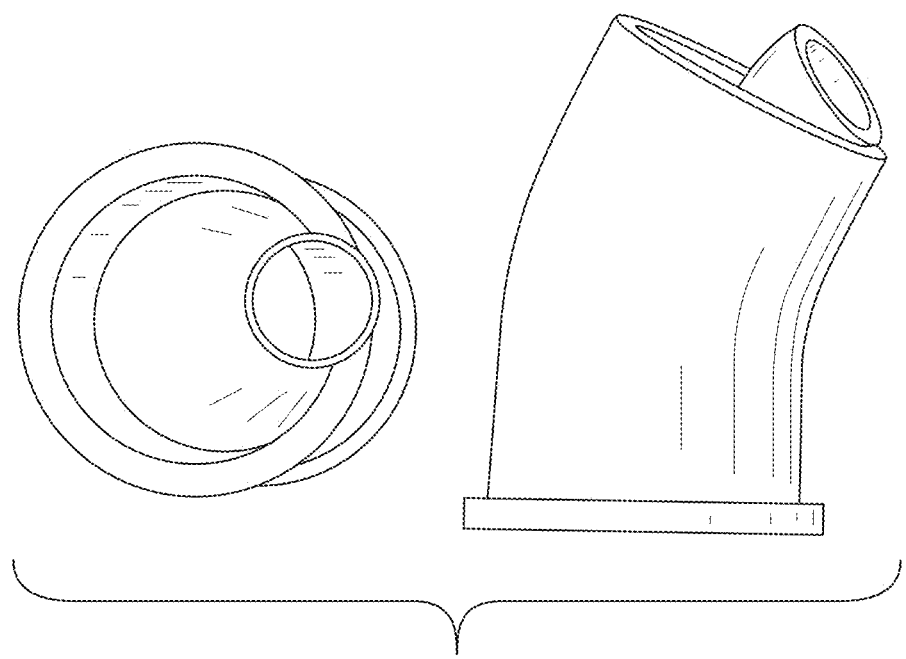
FIG. 11 is a photograph showing a sample nasal plug as shown in FIGS. 7A-7D.

FIG. 11 is a photograph showing a sample nasal plug as shown in FIGS. 7A-7D.

Figure 8A:
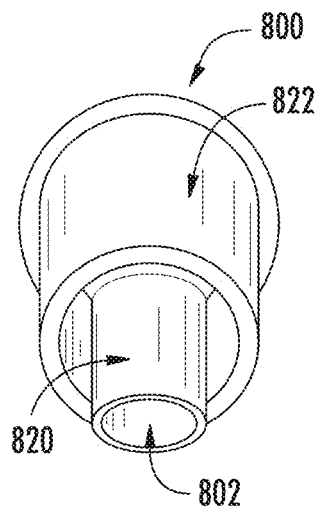
FIG. 8A is a perspective top view of another example nasal plug according to principles described herein.
Figure 8B:
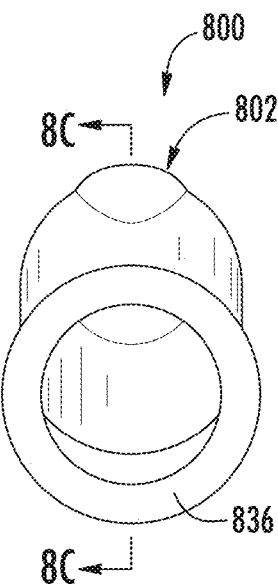
FIG. 8B is a bottom view of the example nasal plug of FIG. 8A.
Figure 8C:
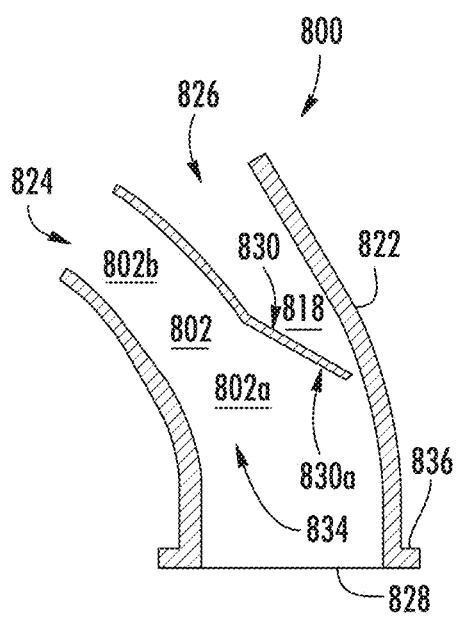
FIG. 8C is a cross-sectional side view of the example nasal plug of FIG. 8A, taken along line A-A of FIG. 8B.
Figure 8D:
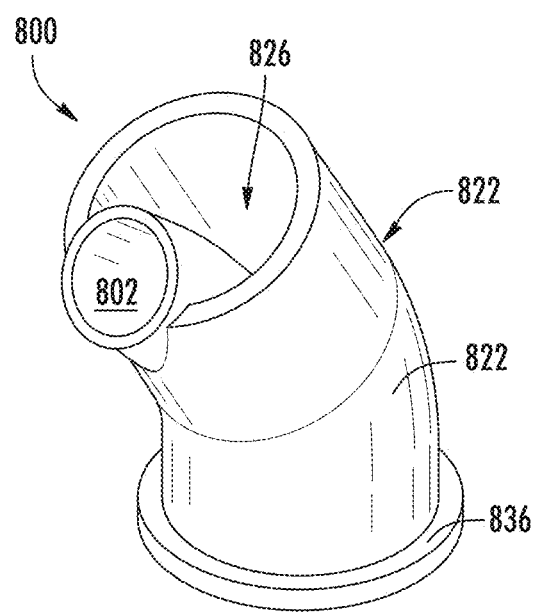
FIG. 8D is a perspective view of the nasal plug of FIGS. 8A-C.

FIG. 8A is a perspective top view of another example nasal plug according to principles described herein. FIG. 8B is a bottom view of the example nasal plug of FIG. 8A. FIG. 8C is a cross-sectional side view of the example nasal plug of FIG. 8A, taken along line A-A of FIG. 8B. FIG. 8D is a perspective view of the nasal plug of FIGS. 8A-C.

The embodiment of the vented nasal plug illustrated in FIGS. 8A-8D includes a cone-like/funnel shaped inner channel 802 captures a larger degree of airflow over the embodiment of FIGS. 4A-D, thereby providing an easier path for the incoming airflow to follow, while maintaining the narrow opening (proximal outlet 824) on the inhalation side (funnel side) of the device. The cone-like inner channel 802 also provides a larger vent opening 818 on the exhalation side (vent side) of the device than the prior described embodiment, allowing a larger amount of airflow to escape out the vent opening. The proximal outlet 824 at the end of the cone-like inner channel may be narrowed in comparison to the uniform channel of FIGS. 3A-3D in order to facilitate a higher exit velocity and increase the stimulation of the air jet.

As shown in FIGS. 8A-8D, the funnel shaped channel 802 includes a cone-shaped/frustoconical portion 802*a* with a wall 830 extending into a larger lumen 832 formed by a wall of a larger tube 822. Unlike the embodiment of FIGS. 5A-5D, the outer larger tube 822 is a "curved cylinder" or an "arched tube". The funnel shaped channel 802 further comprises a tubular channel 802*b* adjacent to and in fluid communication with the frustoconical portion 802*a*. The tubular portion 802*b* may connect with the cone-shaped portion seamlessly to form a continuous lumen between a distal opening 834 of the conical portion and a proximal outlet 824 of the tubular portion, wherein the tubular portion is angled with respect to or curved away from a direction perpendicular to the plane of the distal outlet 828 of the larger tube 820. the proximal outlet 824 of the tubular portion 802*b* of the funnel shaped channel 822 may extend beyond the end proximal outlet 826 of the larger tube 822. While shown as extending beyond the proximal outlet/end of the larger tube 822, the proximal outlet 824 of the tubular portion 802*b* of the funnel shaped channel 822 does not need to extend beyond the end proximal outlet 826 of the larger tube 822 so long as the proximal outlet 824 causes inhaled gas to flow in a direction at an angle with respect to the plane of the proximal outlet 826 of the outer larger tube 822. In the illustrated embodiment, the wall 830 forms an angle of about 75° at rest with respect to the inner surface of the wall of the larger tube 822 on the inhalation side of the tube. The angle may range from 10°-90° without departing from the spirit and scope of the invention. At least part of the outer structure of the funnel-shaped portion may be formed by the wall of outer tube 822.

The wall 830 may flex with respect to the tubular portion 802*b* of the funnel shaped channel 802. For example, the wall 830 may be made of a thin layer of flexible material such as silicon, which may be formed of the same material as the remainder of the vented nasal plug 800. The wall 830 being movable includes a free end 830*a* within the lumen of the outer larger tube 822. In operation, upon inhalation, the free end 830*a* of the wall 830 is moved by pressure created by the patient's inhalation of air thus closing close the vent area 818 by moving the free end 830*a* to abut the inner wall surface of the larger outer tube 822 within the lumen, thus forcing the inhaled air into the channel 802 of the smaller tube 820. Upon exhalation, the free end 830*a* is forced away from the inner wall surface of the larger outer tube by pressure created by patient exhalation such that the vent 818 is opened, allowing exhaled air to pass through both proximal outlets 824 and 826 and into channel 802 and the vent 818, respectively, and into the lumen of the larger tube to the distal outlet 828. Thus, the wall 830 and its free end 830*a* form a passive valve with the lumen of the larger tube.

Also illustrated in FIGS. 8A-8D is an optional lip 836 at the inhalation opening/distal outlet 828 of the nasal plug 800. The lip 836 reduces the risk of accidental aspiration of the nasal plug 800 during use. The lip is configured to "catch" on the opening of the nostrils and also provide an easier grip for the user to manipulate the device.

Similar to the prior designs, the thickness of the tube walls and the angle of the inner cone/curved head can be manipulated to modify the vent opening and the angle of airflow redirection. In the design in FIGS. 8A-8D, a redirection angle of 0°-90° for inhaled air is possible if the nasal aid is inserted fully into the nostril. An example angle of redirection of approximately 45° is illustrated in FIGS. 8A-8D.

The angle may be different or the same for different nostrils in the same patient. For example, the angle may be >20° from a central axis (axial direction) of the nasal plug. The angle may range from about 5° to 90°. At least in some circumstances, the angle should be determined such that the air flow through the passage is directed to a person's lower meatus. That is, the angle of the passage may be in the range of >5°, and in some circumstances, >10°. In addition to the redirecting airflow to therapeutic zones in the nasal mucosa, the nasal plug illustrated in FIGS. 8A-8E serves to maintain the functionality of dilating the frontal nasal valve.

In the embodiment of FIGS. 8A-8D, the funnel portion 802*a* distal opening 834 has periphery that may be spaced away from the distal outlet 828 and well into the lumen of the larger tube 822. The lumen of the outer tube 822 may be narrower than the lumen of the embodiments of FIGS. 6A-6D and 7A-7D. This configuration has advantages for patients with small-sized nostrils/nares.

In FIGS. 6A-6D, 7A-7D and 8A-8D each include curved outer tubes and differ from one another by size of the lumen of the outer tube and the diameter of the inner channel/tube, with the other components proportionally sized. For example, in the illustrative embodiment of FIGS. 6A-6D, the larger outer tube may have an example diameter of approximately 12.7 mm, while the example inner diameter of the inner channel/tube is approximately 4.76 mm; in the illustrative embodiment of FIGS. 7A-7D, the larger outer tube may have an example inner diameter of approximately 10.7 mm, while the example inner diameter of the inner channel/tube is approximately 4.76 mm; and in the illustrative embodiment of FIGS. 8A-8D, the larger outer tube may have an example inner diameter of approximately 8.95 mm, while the example inner diameter of the inner channel/tube is approximately 4.76 mm. These dimensions are meant to be illustrative and not limiting. The diameter of the lumen of the inner tube and the larger outer tube does not need to remain constant along their lengths. In some aspects, the diameter of the lumen of the larger outer tube at its distal end may be greater than the diameter of the lumen of the larger outer tube at its proximal end in any of the described embodiments. Moreover, the inner tubular channel of any of the embodiments may have a larger diameter at its distal end than at its proximal end.

As can be seen in any of the embodiments of FIGS. 4A-4D, 5A-5D, 6A-6D, 7A-7D and 8A-8D, the nasal plug itself may be substantially hollow, formed by a wall layer having a thickness of approximately 0.2 to 3 mm, for example, 2 mm. As can also be seen in any of the embodiments of FIGS. 4A-4D, 5A-5D, 6A-6D, 7A-7D and 8A-8D, the thickness of the wall layer adjacent the conical portion of the funnel may be thicker. The lip of any of the embodiments of FIGS. 4A-4D, 5A-5D, 6A-6D, 7A-7D and 8A-8D may have a thickness in the range of, for example, 1-4 mm inclusive of the wall thickness. The height of the lip may be, for example, in the range of 1-4 mm.

Any of the embodiments described herein may include a thin or very thin layer of flexible material such as silicon to be used for the material for the inner channel/tube. This will allow the inner channel to be extremely reactive to incoming pressure changes. During inhalation, incoming airflow will force open the wide cone opening of the inner channel, capturing most if not all of the flow. However, during exhalation, the pressure against the wall of the inner channel will force it to deform and flatten, increasing the area of the vent opening.

Each of the embodiments herein provides an exit angle of inhaled air flow at a predetermined angle with respect to an axial direction of the nasal plug to provide airflow to the nostril at a predetermined location within the sinuses. In any of the embodiments, the entire channel may at an angle through the entire length of the nasal plug or a portion of the channel, e.g., the proximate portion of the channel, may be angled to provide an exit at the proximate end of the nasal plug at the appropriate predetermined angle α.

The predetermined angle α may be different or the same for different nostrils in the same patient. For example, the angle may be >20° from a central axis (axial direction) of the nasal plug. The angle may range from about 5° to 90°. At least in some circumstances, the angle should be determined such that the air flow through the passage is directed to a person's lower meatus. That is, the angle of the passage may be in the range of >5°, and in some circumstances, >10°.

The designs herein lend themselves to three dimensional (3D) printing as a method of manufacturing, although other techniques such as injection molding and the like may be used to make the nasal plugs described herein. FIG. 9 is a photograph showing the example embodiment of FIGS. 4A-4D manufactured using stereolithography (SLA) printing techniques. FIG. 10 is a photograph showing a sample nasal plug as shown in FIGS. 5A-5D manufactured according to SLA printing techniques.

Besides ENS patients, may different patient populations that can potentially benefit from the redirection of the nasal flow. One example could be septal perforation, i.e., patients who have with a hole in their septum. Common symptoms include dry nose, crusting, pain, bleeding and whistle, usually at the back edge of the perforation. Our study has shown that is where (the back edge) the bulk airflow hit and create a lot of stress. If airflow can be directed from directly hitting the back edge of the perforation, the patient may obtain relief. Additionally, patients with sinus issues may experience relief from redirected airflow provided by the nasal plug according to principles of the present invention.

Other symptoms may be alleviated by nasal plugs according to principles of the present invention, such as nasal dryness/coldness, nasal irritation, nasal crusting, nasal burning, nasal pain, nasal bleeding, feeling of nasal obstruction/congestion, feeling of dyspnea/suffocation, difficult breathing, asthma like breathing, feeling of nose being too open, nasal emptiness, nose feels numb, excessive nasal airflow, disturbed/disorganized airflow, nasal inflammation, increased illnesses from damaged nasal physiology such as recurrent sinus infection; disrupted nasal cycle; hypersensitivity to volatile compounds, reduced sense of smell, impaired nasal drainage, lack of mucus/difficulty removing thick mucus/clearing, sleep deprivation/unable to sleep because of difficulty breathing; anxiety, inability to relax, impaired concentration caused by breathing, chronic fatigue.

A nasal plug according to principles described herein comprise a first tube having a first wall forming a first lumen of a first diameter, the first tube having a first tube proximal end in a proximal plane and a distal end in a distal plane; and a second tube that includes a second wall forming a second lumen of a second diameter, the second diameter smaller than the first diameter, a channel formed by the second lumen and extending from the first tube proximal end into the first lumen of the first tube; a flexible wall having a free end within the first lumen, the flexible wall movable within the first lumen and having a length sufficient to touch a surface of the first lumen and fluidically seal the first lumen between the flexible wall and the surface of the first lumen; and a channel proximal end in a channel proximal end plane, the channel proximal end plane at an angle with respect to the distal plane of the first tube.

In any of the embodiments described herein the second tube may comprise a funnel shape having a tubular channel portion and a frustoconical portion in fluid communication, the frustoconical portion comprising at least portion of the flexible wall.

In any of the embodiments described herein, the first wall may form a portion of the second wall.

In any of the embodiments described herein, the angle may be in the range of 5°-90°: In any of the embodiments described herein, the angle may be in the range of 20°-70°. In any of the embodiments described herein, the angle may be in the range of 30°-60°. In any of the embodiments described herein, the angle may be in the range of 45°-55°.

In any of the embodiments described herein, the first tube may have a curved profile from the first tube proximal end. In any of the embodiments described herein, the first tube may have a curved profile from the first tube proximal end to the distal end.

The nasal plug of any of the preceding claims, wherein the first wall has a wall thickness of approximately 1 mm.

In any of the embodiments described herein, the first diameter may be in a range of 8 mm-13 mm. In any of the embodiments described herein, the second diameter may be approximately 5 mm. In any of the embodiments described herein, the second diameter may be approximately 4.76 mm. In any of the embodiments described herein, may include a lip surrounding the distal end of the first tube.

In any of the embodiments described herein, airflow from the distal end causes the flexible wall to touch the surface of the first lumen and fluidically seal the first lumen between the flexible wall and the surface of the first lumen and to divert airflow into the channel formed by the second lumen and out the channel proximal end at an angle with respect to the distal plane.

In any of the embodiments described herein, airflow from the first tube proximal end causes the flexible wall to move away from the surface of the first lumen open a vent between the flexible wall and the surface of the first lumen.

A kit according to embodiments described herein may include two nasal plugs as described herein wherein each of the two nasal plugs are independent from one another such that first channel proximal end and the second channel proximal end are capable of being oriented in in different orientations.

In another aspect, a nasal plug according to principles described herein may include a deformable plug having a first end and a second end and a cross-section sized and shaped to be accepted into and to fluidically seal a person's nasal nares; an axis defined from the first end to the second end; and a passage defined through the deformable polymer from the first end to the second end, the passage having a distal end and a proximal end, wherein the proximal end of the passage is offset from the axis by an angle α, where α>5°, the deformable plug having a frustoconical proximal portion.

A method according to principles described herein may improve nasal sensory perception in a patient and include applying a nasal plug having an outer tube and an inner tube within a lumen of the outer tube, the inner tube having a flexible movable wall; upon inhalation of the patient, air flow causing the flexible movable wall to move within the lumen of the outer tube to block air flow through at least a part of the outer tube and directing substantially all air flow into a lumen of the inner tube to exit at a predetermined location with the patient's nasal cavity; and upon exhalation of the patient, air flow causing the flexible movable wall to move wall within the lumen of the outer tube to cause air flow to pass through both the lumen of the inner tube and the lumen of the outer tube.

In another aspect, air flow exiting the inner lumen upon the inhalation of the patient exits the inner lumen at an angle with respect to direction perpendicular to an axial direction of the outer tube, wherein the angle is between approximately 0°-90°.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A nasal plug, comprising:
   a first tube having a first wall forming a first lumen of a first diameter, the first tube having a first tube proximal end in a proximal plane and a distal end in a distal plane; and
   a second tube, comprising:
      a second wall forming a second lumen of a second diameter, the second diameter smaller than the first diameter,
      a channel formed by the second lumen and extending from the first tube proximal end into the first lumen of the first tube;
      a flexible wall having a free end within the first lumen, the flexible wall movable within the first lumen between (i) an inhalation configuration wherein the free end of the flexible wall moves to touch a surface of the first lumen and fluidically seal a vent area of the first lumen from the channel formed by the second lumen, and (ii) an exhalation configuration wherein the free end of the flexible wall is forced away from the surface of the first lumen to allow airflow through both the first lumen and the second lumen; and
      a channel proximal end in a channel proximal end plane, the channel proximal end plane at an angle with respect to the distal plane of the first tube.

2. The nasal plug of claim 1, the second tube comprising a funnel shape having a tubular channel portion and a frustoconical portion in fluid communication, the frustoconical portion comprising at least a portion of the flexible wall.

3. The nasal plug of claim 1, wherein the first wall forms a portion of the second wall.

4. The nasal plug of claim 1, wherein the angle is in the range of 5°-90°.

5. The nasal plug of claim 1, wherein the angle is in the range of 20°-70°.

6. The nasal plug of claim 1, wherein the angle is in the range of 30°-60°.

7. The nasal plug of claim 1, wherein the angle is in the range of 45°-55°.

8. The nasal plug of claim 1, wherein the first tube has a curved profile from the first tube proximal end.

9. The nasal plug of claim 1, wherein the first tube has a curved profile from the first tube proximal end to the distal end.

10. The nasal plug of claim 1, wherein the first wall has a wall thickness of approximately 1 mm.

11. The nasal plug of claim 1, wherein the first diameter is in a range of 8 mm-13 mm.

12. The nasal plug of claim 1, wherein the second diameter is approximately 5 mm.

13. The nasal plug of claim 1, wherein the second diameter is approximately 4.76 mm.

14. The nasal plug of claim 1, further comprising a lip surrounding the distal end of the first tube.

15. The nasal plug of claim 1, wherein the airflow from the distal end causes the free end of the flexible wall to touch the surface of the first lumen and fluidically seal the vent area of the first lumen to divert the airflow into the channel formed by the second lumen and out the channel proximal end at the angle with respect to the distal plane.

16. The nasal plug of claim 1, wherein the airflow from the first tube proximal end causes the flexible wall to move away from the surface of the first lumen to open the vent area between the flexible wall and the surface of the first lumen.

17. A kit for reducing nasal discomfort, the kit comprising:
   two nasal plugs, each nasal plug comprising:
      a first tube having a first wall forming a first lumen of a first diameter, the first tube having a first tube proximal end in a proximal plane and a distal end in a distal plane; and
      a second tube, comprising:
         a second wall forming a second lumen of a second diameter, the second diameter smaller than the first diameter,
         a channel formed by the second lumen and extending from the first tube proximal end into the lumen of the first tube;
         a flexible wall having a free end within the first lumen, the flexible wall movable within the first lumen between (i) an inhalation configuration wherein the free end of the flexible wall moves to touch a surface of the first lumen and fluidically seal a vent area of the first lumen from the channel formed by the second lumen, and (ii) an exhalation configuration wherein the free end of the flexible wall is forced away from the surface of the first lumen to allow airflow through both the first lumen and the second lumen; and
         a first channel proximal end in a channel proximal end plane, the first channel proximal end plane at an angle with respect to the distal plane of the first tube; and
   wherein each of the two nasal plugs are independent from one another such that the first channel proximal end and the second channel proximal end are capable of being oriented in in different orientations.

18. The nasal plug of claim 17, further comprising a first lip surrounding the distal end of each of the first tubes.

* * * * *

UNITED STATES PATENT AND TRADEMARK OFFICE
CERTIFICATE OF CORRECTION

| | | |
|---|---|---|
| PATENT NO. | : 12,324,764 B2 | Page 1 of 1 |
| APPLICATION NO. | : 17/801154 | |
| DATED | : June 10, 2025 | |
| INVENTOR(S) | : Zhao et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 319 days.

Signed and Sealed this
Third Day of February, 2026

John A. Squires
*Director of the United States Patent and Trademark Office*